United States Patent
Gittleman (10) Patent No.: US 6,991,461 B2
(45) Date of Patent: Jan. 31, 2006

(54) EXPANDABLE DENTAL IMPLANT APPARATUS

(76) Inventor: Neal B. Gittleman, 15 Greenway Plz., Houston, TX (US) 77046

( * ) Notice: Subject to any disclaimer, the term of this patent is extended or adjusted under 35 U.S.C. 154(b) by 200 days.

(21) Appl. No.: 10/034,538

(22) Filed: Dec. 28, 2001

(65) Prior Publication Data

US 2003/0124488 A1    Jul. 3, 2003

(51) Int. Cl.
*A61C 8/00* (2006.01)
(52) U.S. Cl. .................................................. 433/173
(58) Field of Classification Search ................ 433/172, 433/173, 174, 175, 176
See application file for complete search history.

(56) References Cited

U.S. PATENT DOCUMENTS

| | | | | |
|---|---|---|---|---|
| 3,708,883 A | * | 1/1973 | Flander ...................... 433/174 |
| 5,004,421 A | * | 4/1991 | Lazarof ...................... 433/173 |
| 5,611,688 A | * | 3/1997 | Hanosh ...................... 433/173 |
| 5,667,384 A | * | 9/1997 | Sutter et al. .................. 43/173 |
| 5,681,167 A | * | 10/1997 | Lazarof ...................... 433/173 |
| 6,039,568 A | * | 3/2000 | Hinds ......................... 433/173 |
| 6,227,860 B1 | * | 5/2001 | Hobo ......................... 433/173 |
| 6,332,778 B1 | * | 12/2001 | Choung ...................... 433/172 |
| 6,350,126 B1 | * | 2/2002 | Levisman ...................... 433/1 |

FOREIGN PATENT DOCUMENTS

DE           197 05 571 A1 *  9/1998

* cited by examiner

*Primary Examiner*—Cary E. O'Connor (57) ABSTRACT

A novel dental implant with flexible expansion ribs that lock into and compress the bone within a drilled hole in the jawbone. Upon tightening the screw used to mount the implant abutment, a set of thin medical-alloy ribs lock into the surrounding bone to provide an immediate and permanently strong support for a dental prosthesis while bone growth into the implant occurs. The expanding ribs turn an edge outward to lock into the surround bone and preventing the rotation of the implant assembly during installation and use.

7 Claims, 14 Drawing Sheets

EXPANDABLE DENTAL IMPLANT APPARATUS

BACKGROUND OF THE INVENTION

Dental implants, acting primarily as a replacement for the root portion of the tooth, should offer the strongest bond possible with the underlying bone. Present methods rely upon drilling a cylindrical hole of desired depth and setting by means of spiral threads, slip-fit or press-fit a cylindrical implant. In the case of the slip-fit, time must be allowed for new bone to grow into recesses on the implant before any chewing pressure can be applied. The press-fit offers a better load bearing but still requires healing time. Flared-top or stepped cylinders give protection against occlusal pressure driving the implant further into the bone than is desired. The externally threaded, stepped implant offers yet a better grip within the bone at the expense of the removal of more of the original bone and the trauma of the self threading or pre-threading of the prepared hole in the jawbone. A threaded insert requires that the hole be of circular cross-section. Often the thread is within the weaker cancelous portion of the bone and requires a greater healing time for bone to grow into the implant.

The apparatus described herein offers a locking means and a bone condensing means with advantages over the prevailing art.

DETAILED DESCRIPTION OF THE DRAWINGS

Figure 1:
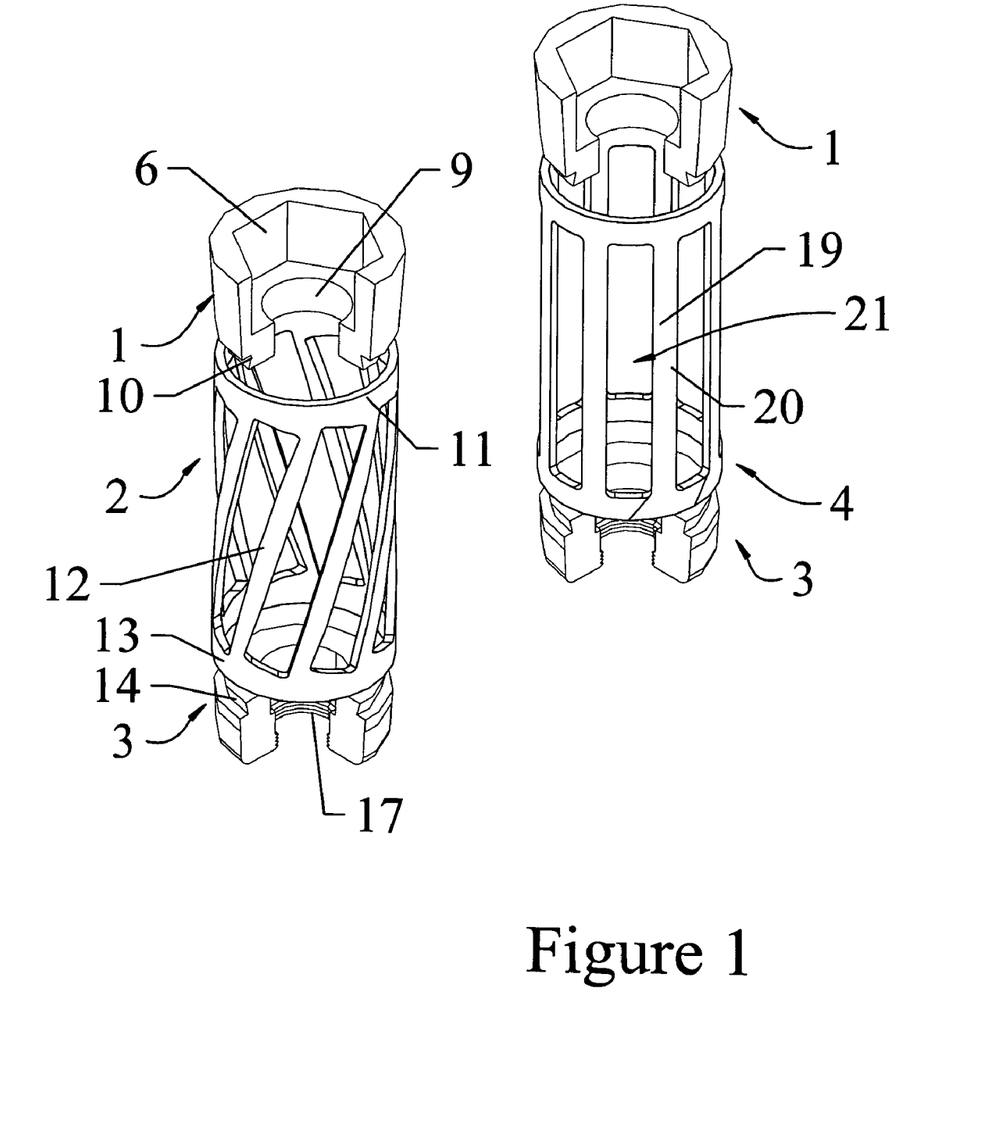
FIG. 1 gives a perspective views of two expansion implants with partial cutaways.
Figure 9:
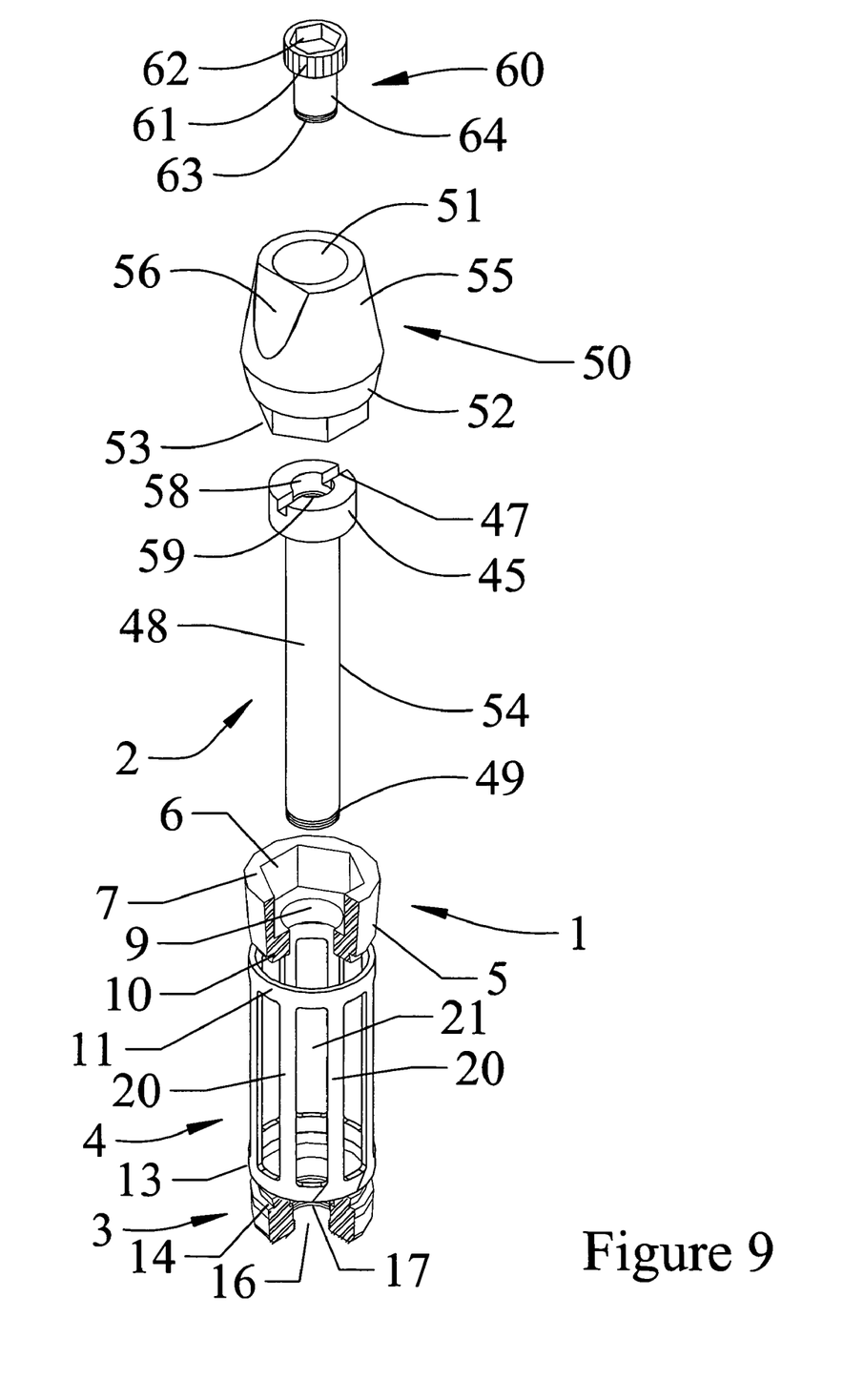
FIG. 9 shows a perspective view of the dental implant with typical abutment and machine screws.

The dental implant envisioned in this invention is formed from three sections: an upper conformal socket 1 to accommodate a dental abutment, an expansion tube 2 and a lower retention nut 3, as detailed in FIG. 1 and FIG. 9. The expansion tube is manufactured by chemically milling open slots in a thin-walled titanium medical-alloy tube leaving straight ribs 20 or spiral ribs 12. Circumferential ends 11 and 13 of the tube are joined to upper conformal socket 1 and lower retention nut 3 by suitable means. In the embodiment shown, an undercut radial groove 10 is made in the upper socket 1 around the base and the upper lip 11 of the tube is forced onto or swaged into the groove 10. The same method is used to join nut 3 to the bottom flange 13 of expansion tube 2. Means to prevent the mutual rotation of these elements such as ribs, flats, dimples or projections are shown as a flattened areas 14 on the surface of nut 3. In the manufacturing process, the top 11 of the expansion tube 4 is forced or formed over a recessed groove 10 in the upper socket element 1. The lower end 13 of the expansion tube 4 is fixed over a similar recessed groove around the upper end of retaining nut 3. To prevent any relative twisting motion between the upper socket and the expansion tube and between the expansion tube and the lower retaining nut, anti-rotational elements are formed in the tube ends. Flats 14 on the retaining nut 3 prevent tube end 13 from rotating around nut 3.

The same anti-rotational elements are used to secure the upper conformal socket 1 within the upper end 11 of the expansion tube 4. Alternate means of securing the thin walled tube to the nut and upper socket include dimpling the tube into recesses, laser welding and other methods known to those skilled in the art of metal joining.

Photo-chemical milling is a process of coating the metal object with a thin layer of a photosensitive liquid polymer know as a photoresist. Upon drying, the photoresist is exposed to ultra-violet light through an appropriate mask such as a positive, black-and-white film image of the desired pattern. Where the light falls upon the object through the mask, the photoresist is hardened. The photoresist is then developed to wash away the unhardened portion. The exposed bare metal of the object is thinned or etched away by submersion in a bath of chemical milling agents. Other means of machining the slots include abrasive milling and laser cutting.

Expansion tube 4 is shown with straight, non-spiral sides as detailed in FIG. 9. The hollow through space 21 allows an implant mounting screw 54 to enter the through-hole 9 of the upper conformal socket 1 and engage with threads 17 in the retention nut 3. These threads can be of the interference or locking type to aid in the screw retention within the nut thread 17. The implant expansion screw 54 is shown with a typical machine head 45 with a cylindrical recess 58 having internal threads 59 and slotted drive means 47 to accommodate a screwdriver or other driving means. Shaft 48 terminates in a spiral thread 49. The thread can extend for a further distance up the shaft 48 than illustrated in the figures. Shaft 48 can be coated with an adherent layer of hydroxyapatite, bone-growth media to help in incorporating new bone. A typical abutment 50 having a counter-sunk, cylindrical through hole 51 is large enough to allow the passage of screw shaft 64 of an abutment mounting screw 60 while preventing the machine screw head 61 from penetrating below the counter-sink. Abutment taper 55 and alignment flat 56 mate with the underside of a typical dental prosthesis (not shown).

In order to facilitate the removal of abutment 50 from the upper conformal socket 1 of the implant, internal threads in recess 51 (not shown) can be used to raise the abutment from the implant by means of a special pusher tool with external threads to engage these abutment threads and a bearing end to push against the top of head 45 of the implant expansion screw 2.

The abutment mounting screw shaft 64 passes through the abutment through-hole 51, threading into the top internal thread 59 in cylindrical recess 58 in the top of implant holding screw 54 to fix the abutment to the expanded implant assembly. The threaded end 63 of the screw shaft can be equipped with locking threads with an interference fit to prevent the two screws from separating. Hex projection 53 which mates with hexagonal recess 6 of upper conformal socket 1 prevents the abutment from rotating with respect to implant assembly. Projection 53 and recess 6 have a mating taper to provide a locking interference fit, much like the well known Morse taper.

Figure 2:
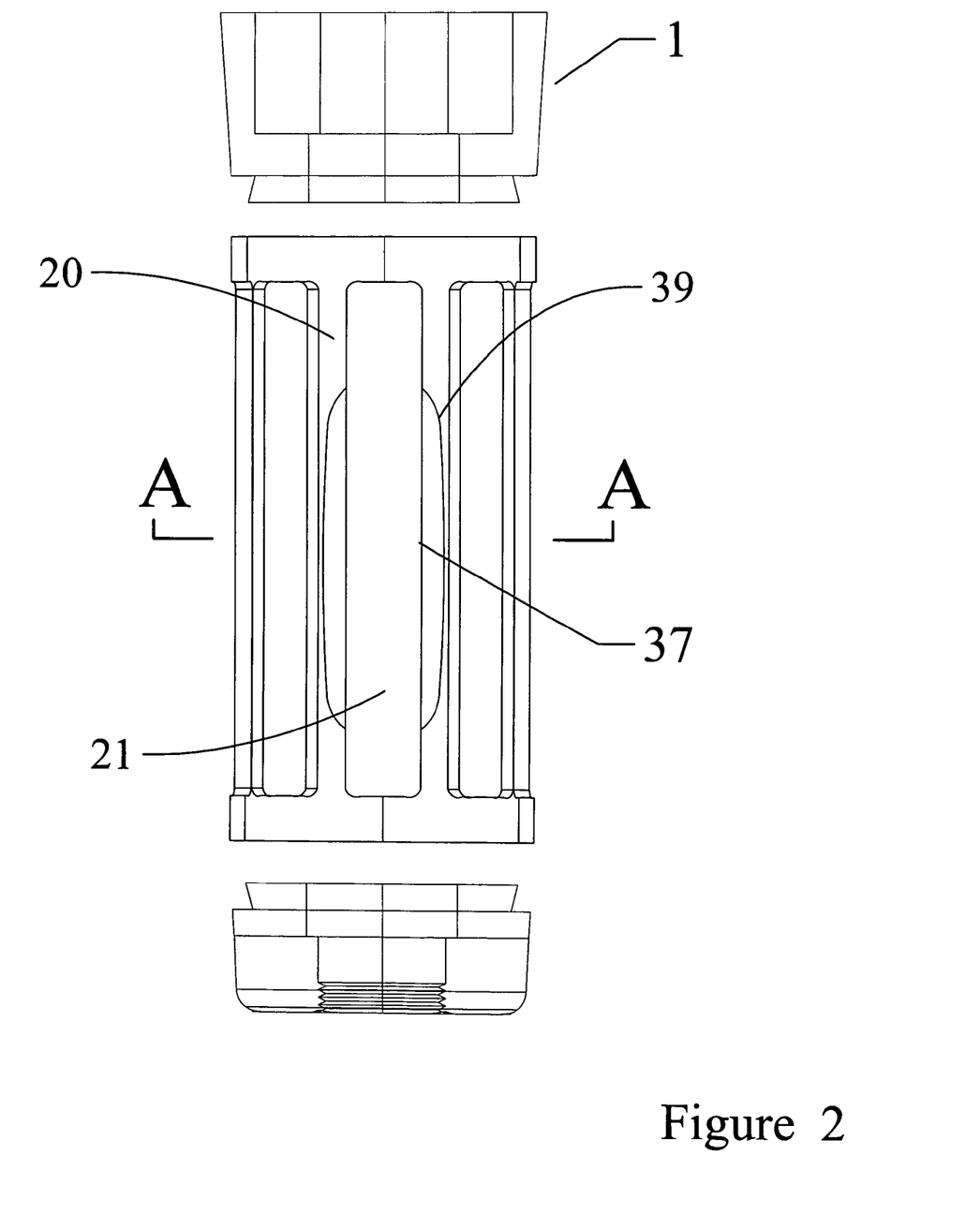
FIG. 2 is an elevated front view of an expansion implant.
Figure 3:
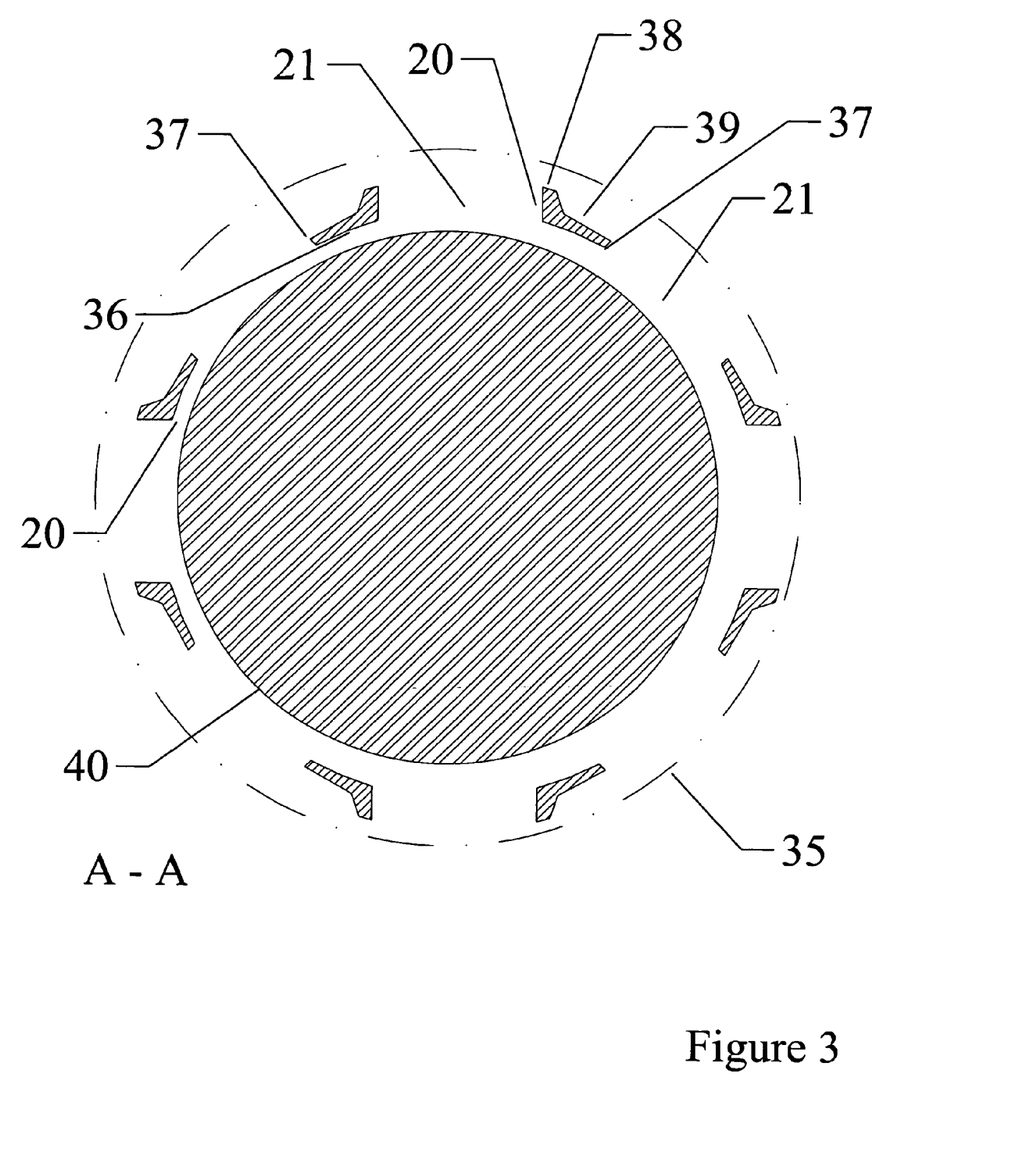
FIG. 3 is a horizontal cross section through the expansion implant ribs in the unexpanded position.
Figure 4:
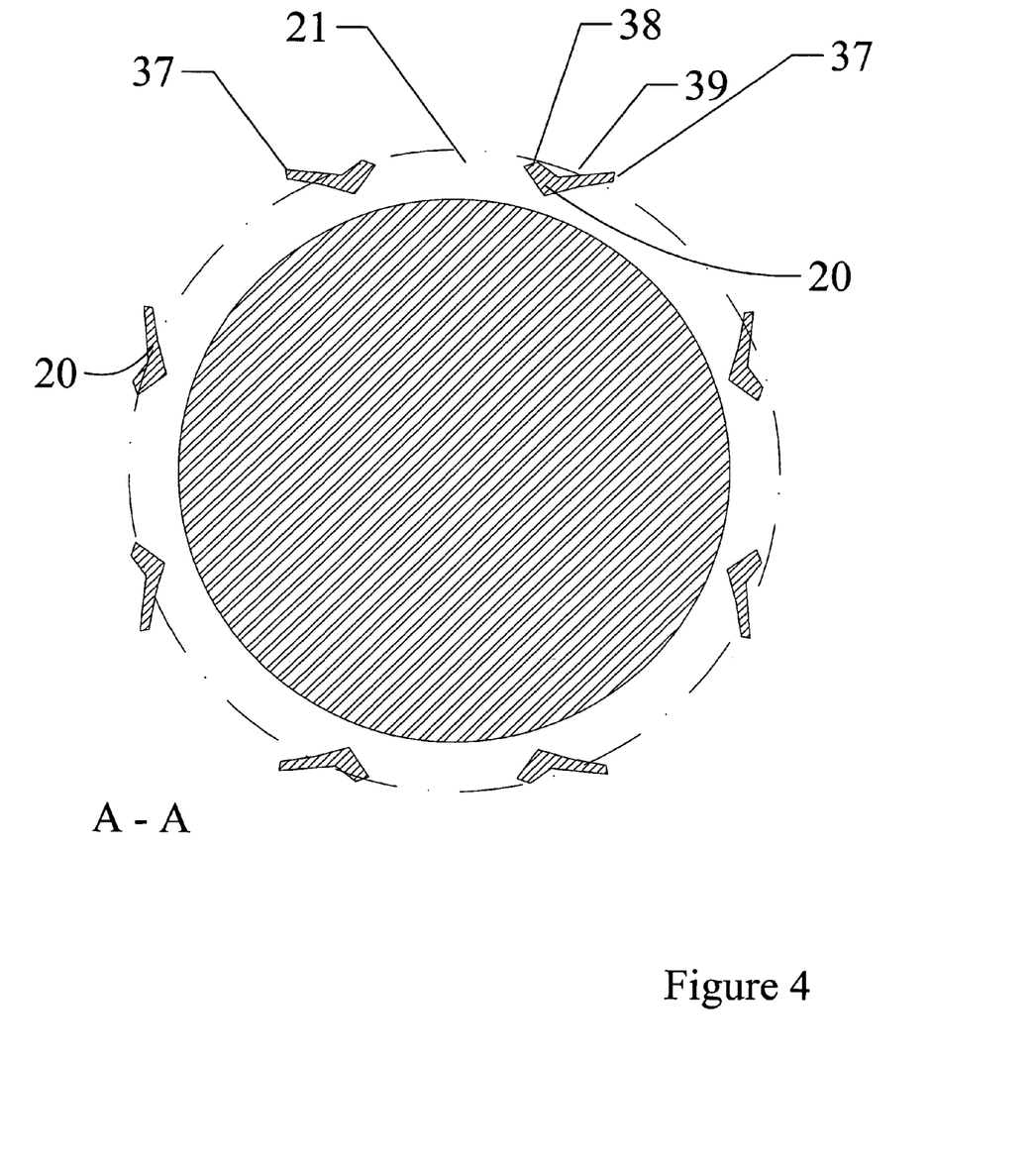
FIG. 4 is the same horizontal cross section through the implant ribs in the expanded and everted or turned out position.

To anchor the implant within a predrilled hole in bone, the abutment screw 54 is tightened, drawing closer together conformal socket 1 and threaded nut 3 and forcing ribs 20 to bow outward to lock the implant into the bone. Compression along the major axis of the expansion tube forces the ribs to bow outward. These ribs constitute the expandable sides of the expansion tube. The nature of the outward expansion of the ribs can be determined by the shape and thickness of the ribs. Indeed, portions of the ribs can be thinned or slotted by chemical milling to result in more curvature during tightening. FIG. 2 details the thinned edge 37 which will bow or fan outward more than the thicker edge 38, locking the ribs into the bone to prevent rotation of the implant assembly. Alternate ribs can be thinned on alternate edges and alternately fanning out in both clockwise and counter-clockwise directions to prevent rotation in either direction as detailed in FIG. 3 and FIG. 4. FIG. 3 shows cross section A—A of the expansion tube 4 in the unexpanded position within the perimeter of drilled hole 35. FIG. 4 shows the same cross section A—A with the expansion tube 4 in the expanded position with edges 37 of the ribs 20 bowed outward and biting into the inner surface of cylindrically drilled hole 35. Since the rib edge 37 is thinner than the rib edge 38, it flexes outward or everts.

A manufacturing technique suitable to the construction of the tube element 4 of the implant is available from Buckbee-Mears, of St. Paul, Minn., (tel: 651 228 6400). They are equipped to photo-machine titanium in thin sheets or in formed pieces. They have a capability to photo-machine 3D parts. Starting with a cylinder (made from a thin-walled tube section) of medical titanium alloy, slots are photochemically machined and portions of ribs are thinned to make the expansion edges 37.

FIG. 2 is a front elevation view of the dental implant described in FIG. 1 with the addition of a thinned sections 39 on two of the front ribs 20 shown. These thinned portions are accomplished by chemical milling through some of the rib thickness in a controlled manner. By controlling the time and temperature in a chemical etching bath, the thickness and consequently the flexibility of the outer edge of the rib are predetermined. The thinned edges 37 will flex toward the viewer more that the thicker edge 38. Eight ribs are viewed in cross section A—A, as in FIG. 3 and FIG. 4. A typical rib 20 has a thinned section 39 with a thin edge 37 and an unetched thick section 38 and an unmodified back 36. The predrilled hole in the bone is represented by circle 35. When the central abutment mounting screw is tightened, the expansion tube ribs 20 bow outward to lock into the sides of the predrilled hole. These expanding tube ribs will condense the cancelous bone and by placing force on the bone, act to enhance further bone growth. A typical unexpanded diameter for this implant is 3.0 mm with an expanded diameter of 3.3 mm.

By allowing some ribs to be wider than others, controlled amounts of pressure can be applied to different sectors of the predrilled hole. In this manner, more pressure can be applied in the labial direction or in the lingual direction to move a surgically sectioned flap of bone in a preferred direction to improve bone mass or position.

Figure 5:
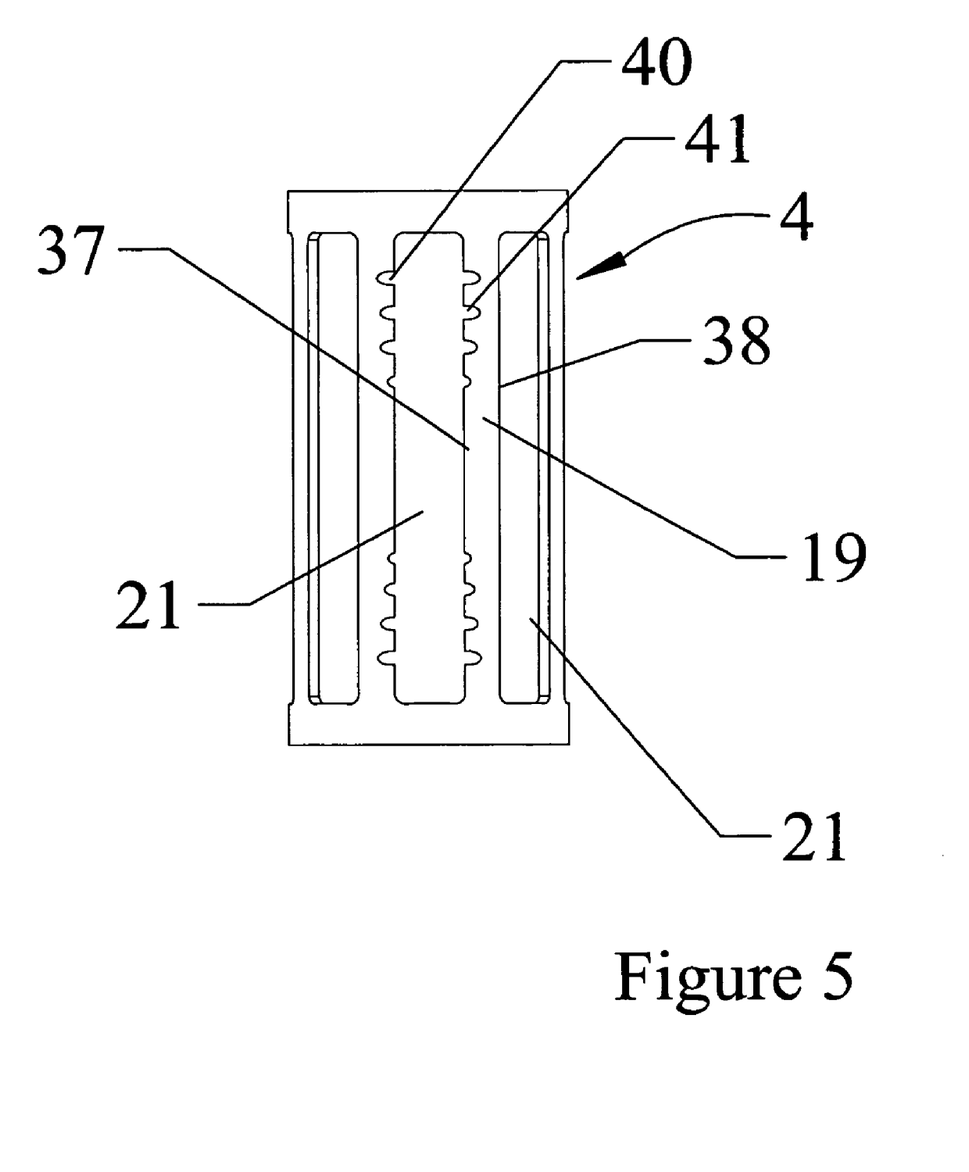
FIG. 5 shows an elevated front view of an expansion implant with notched ribs.
Figure 6:
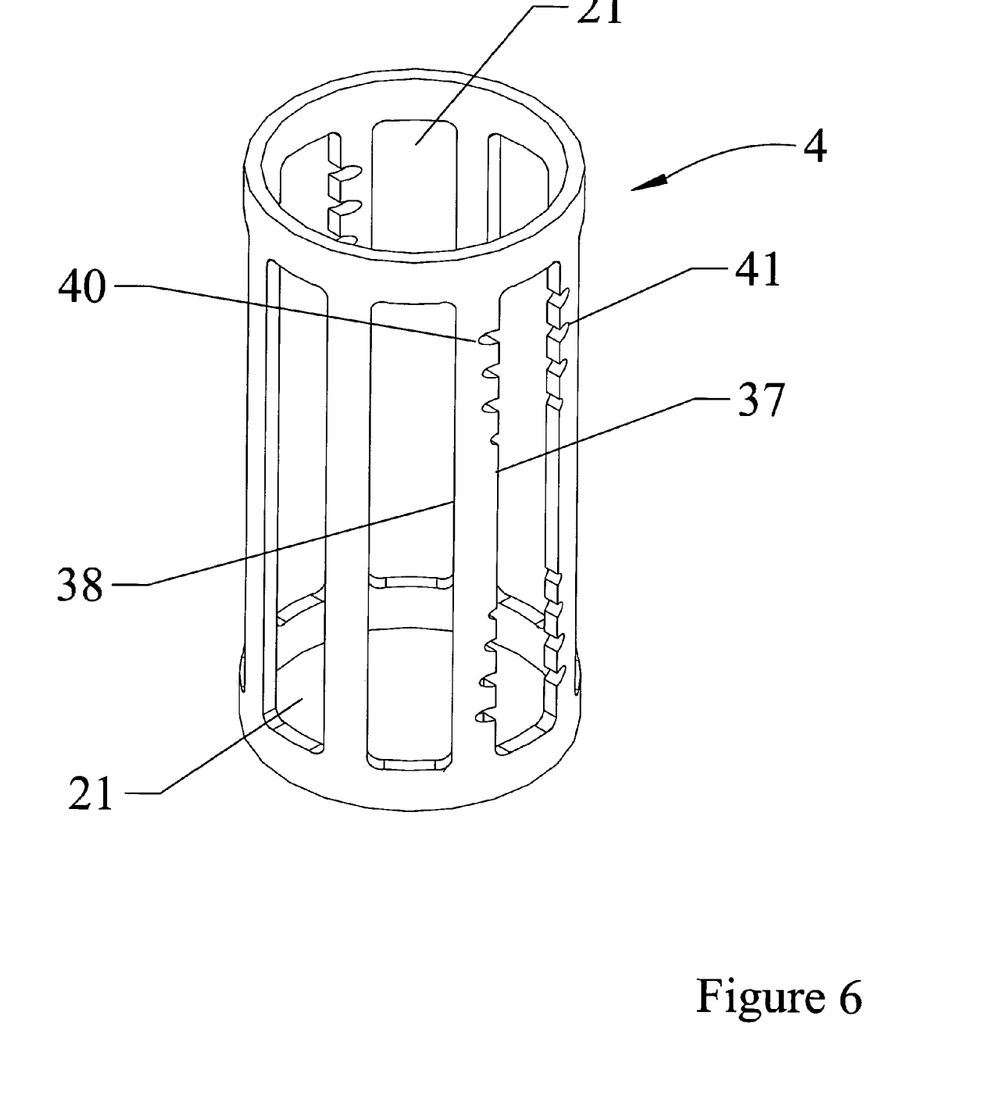
FIG. 6 gives a perspective view of the same expansion implant with several notched ribs.

Another method of modifying the flexibility of portions of each rib is detailed in FIGS. 5 and 6. Rib 19 is shown with a series of notches 40 and 41 placed along rib edge 37 while edge 38 is left unmodified. These notches increase the flexibility of rib 19 in the area of the notches and edge 37 everts or turns outward upon the expansion of tube 4. This eversion or outward turning of edge 37 locks the tube within the predrilled hole in the bone preventing linear or radial motion of the implant.

Figure 7:
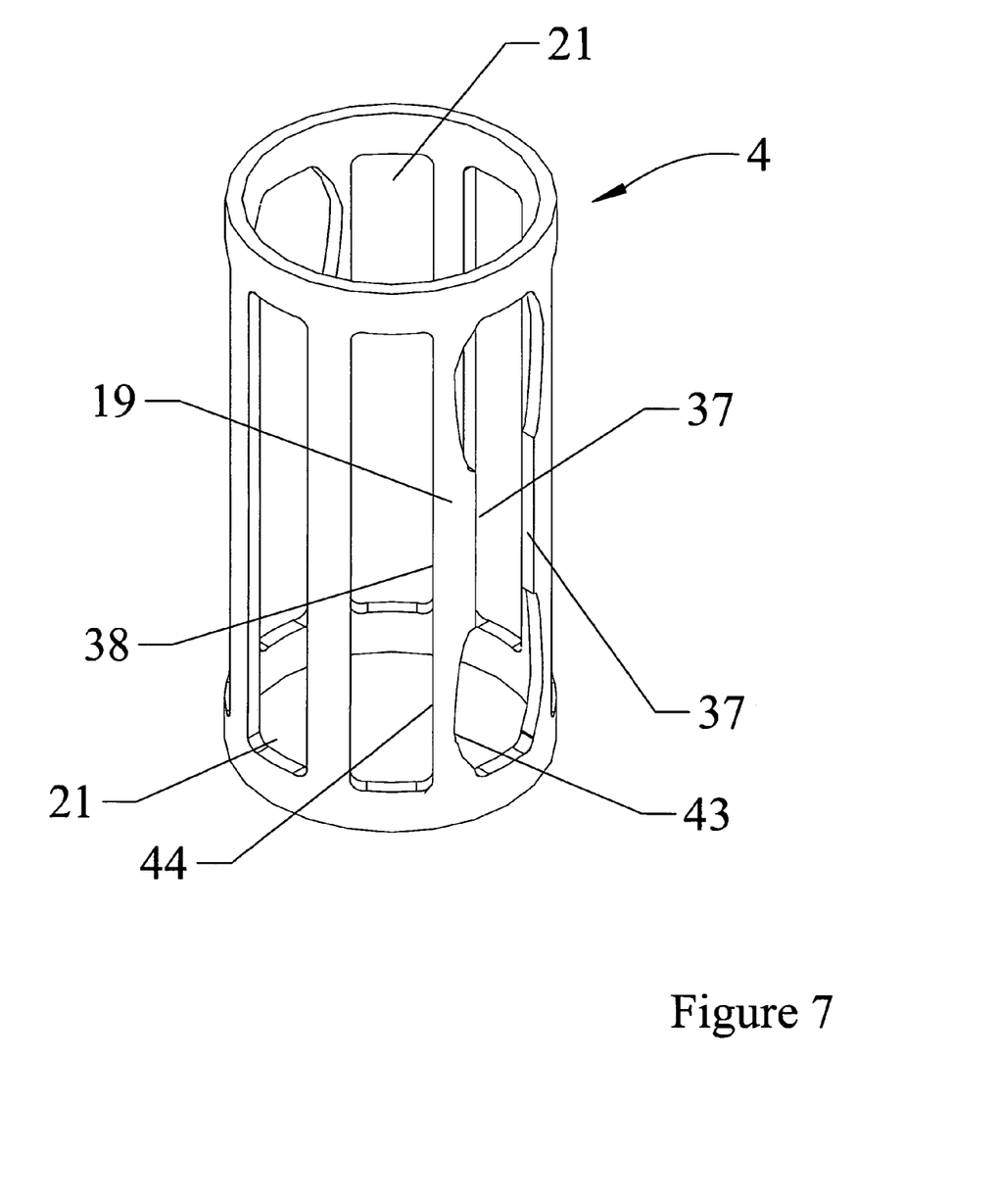
FIG. 7 shows a perspective of the expansion implant cage with some ribs narrowed for increased selective flexibility and bending under compression.
Figure 8:
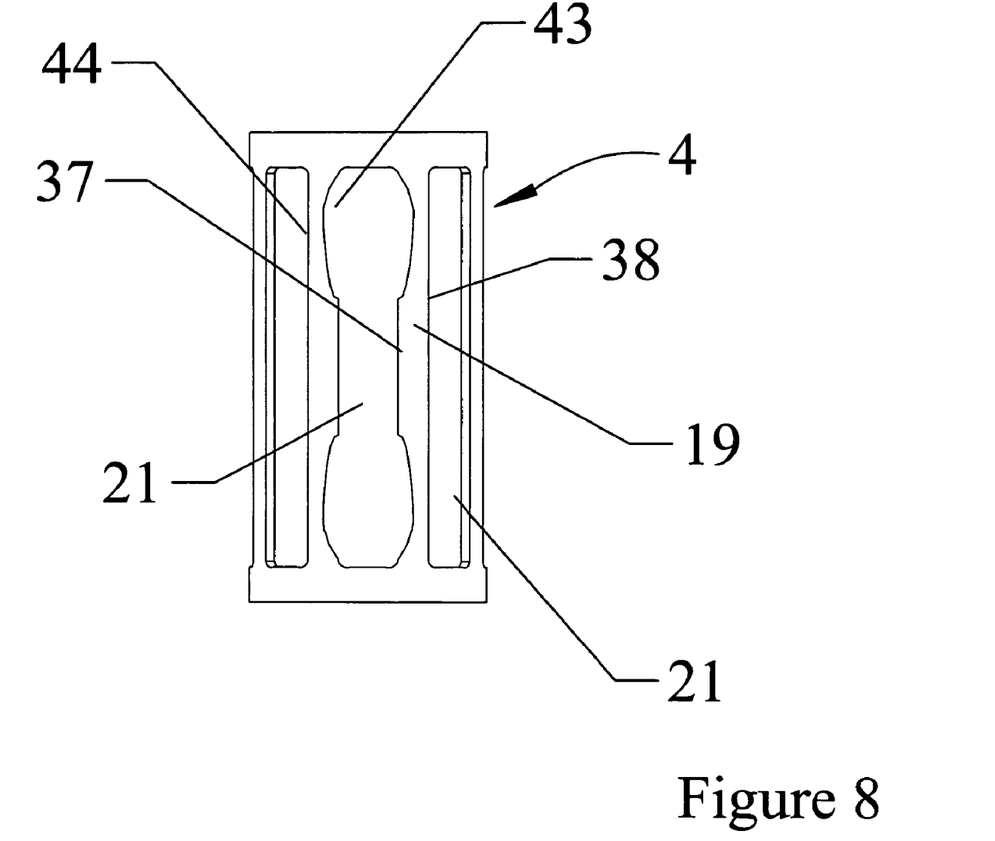
FIG. 8 shows an elevated view of the expansion implant cage with some ribs narrowed for selective flexibility and bending under compression.

FIGS. 7 and 8 offer another embodiment of the invention in which the rib 19 is thinned by removal of metal at point 43. The flexibility of rib 19 is increase between edge 44 and point 43. Rib Edge 37 flexes outward more than edge 38 and locks into a predrilled hole in the bone in such manner as to prevent rotation. In these outwardly expanding ribs, the narrowed portions on ribs will bow with a smaller radius than the unnarrowed portions of the ribs resulting in a somewhat flattened portion of the rib bearing against the inner surface of the hole in the bone parallel to the major axis of the implant, offering a more uniform application of outward pressure to prevent rotation of the dental implant during installation and use.

Figure 10:
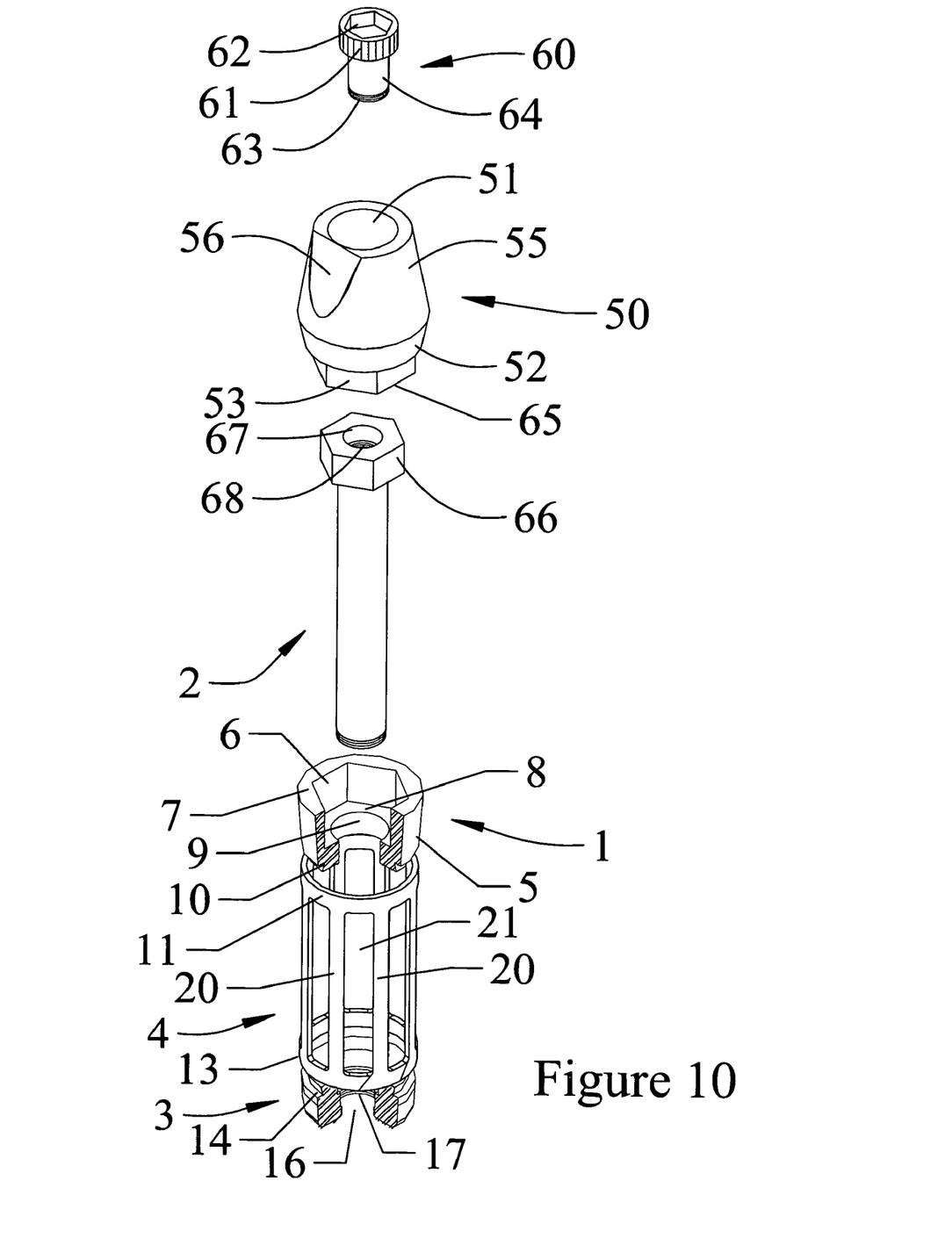
FIG. 10 shows an exploded perspective view of the dental implant with hex headed retaining screw.

FIG. 10 embodies several features to prevent the implant screw 2 from loosening. Hex head 66 is of small enough diameter to be installed and turned within recess 6 of upper conformal socket 1 with a hand or torque wrench. Marks on the wrench and the upper conformal socket allow the retaining screw to be properly positioned. Abutment 50 has a tapered hexagonal recess 65 located on the underface of hexagonal projection 53 that cups over the hexagonal head of the implant screw preventing this recessed screw from rotating while the abutment is in place. The implant screw is installed and turned with the hexagonal faces 66 parallel to the hexagonal inner walls of recess 6. The hexagonal screw head is tapered and the act of placing the abutment will adjust the screw to the proper final locked position. Abutment retaining screw 60 is inserted into through-hole 51 in the abutment and thread 63 of shaft 64 threads into cylindrical hole 67 with internal thread 68 in implant screw 2. Hexagonal recess 62 accommodates a wrench to set this abutment screw in place. The threads 63 and recessed threads 68 can be designed with a locking interference fit.

Figure 13:
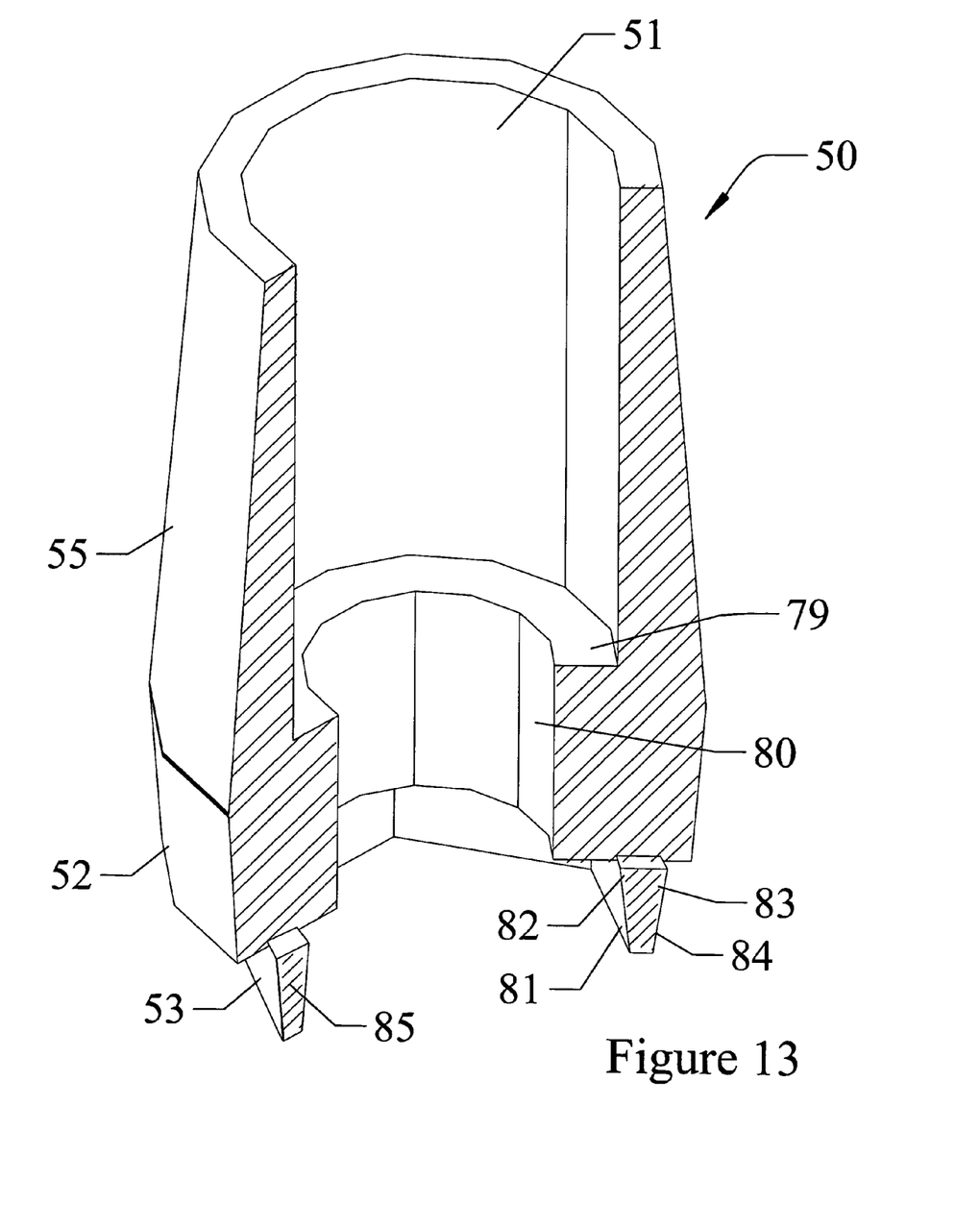
FIG. 13 a sectioned view of abutment with tapered hexagonal base.

FIG. 13 details a cross sectional view of a typical abutment 50 used in this application. Counter sunk through-hole 51 has a shelf 79 and narrower diameter opening 80 to accommodate abutment retaining screw 60. External taper 55 fits within a typical prosthesis (not shown). Emergence taper 52 provides a smooth transition between the implant through the soft tissue. Hexagonal projection 53 cups over the hexagonal head of implant screw 2 and mates within hexagonal recess 6 of upper conformal socket 1 of the implant. This hexagonal projection has internal and external tapered walls shown in cross section 85. The thickness through the wall in the area between 82 and 83 is greater than the thickness through the area between 81 and 84. As the abutment is seated in place, some self-alignment of the abutment, implant mounting screw and implant occurs forming a cohesive, sturdy structural unit.

Figure 11:
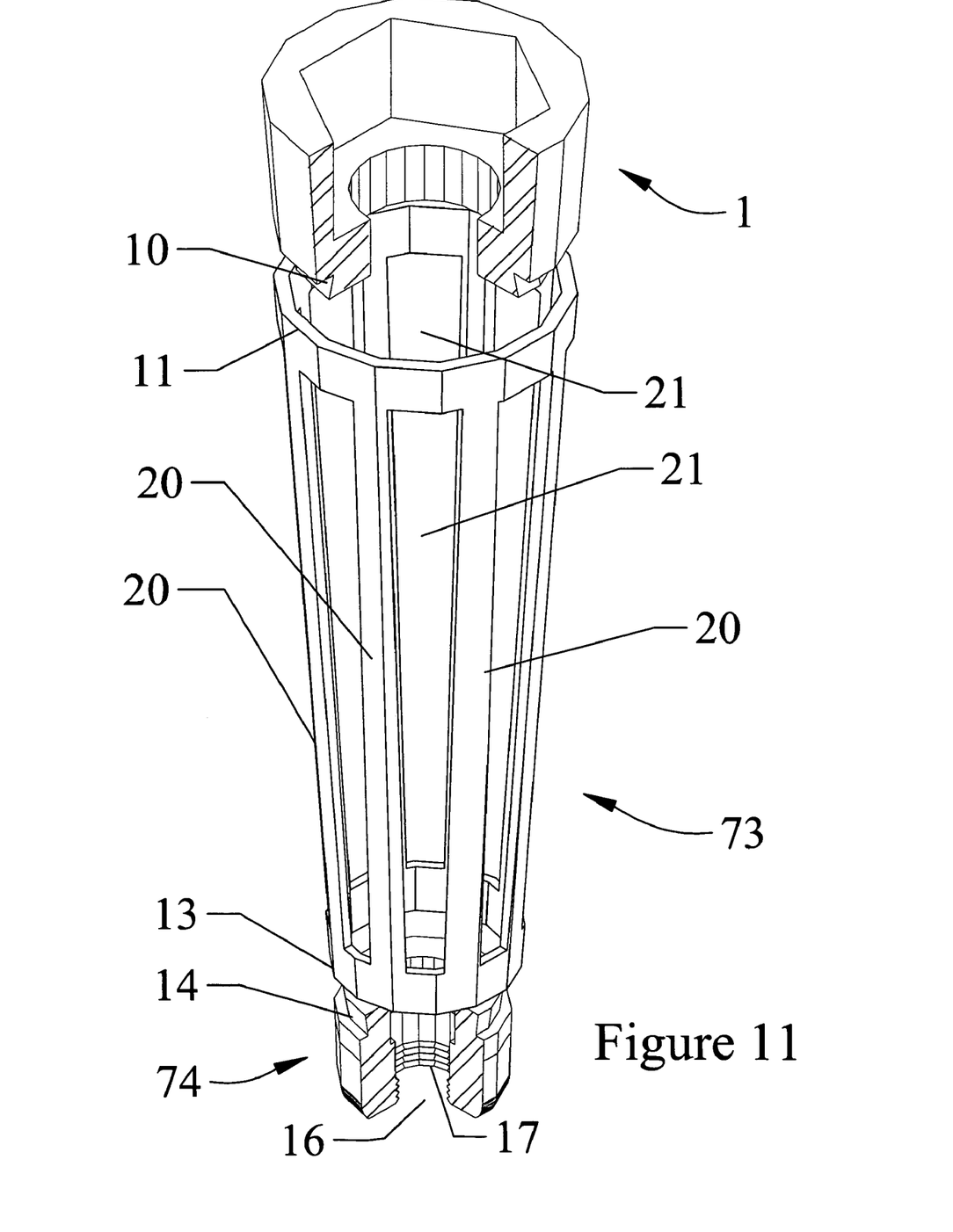
FIG. 11 shows a conical root form expansion tube.

The expansion tube can be fabricated as a truncated conic hollow tube with etched ribs to more closely mimic the taper of the natural tooth root. FIG. 11 details a truncated conical expansion tube 73 with ribs 20 alternated with open spaces 21. Conformal upper socket 1 and lower retaining nut 74 are secured to their respective ends of conical tube 73. The larger upper end 11 of the conical tube is machine forced into groove 10 while the smaller diameter end 13 is forced into groove 14 on the lower retaining nut to form a cohesive unit. Ribs 20 can be equipped with vanes, notches, through-holes and thinned sections as described in other embodiments of this invention. The upper circumference 111 need not be round, but can more closely mimic the profile of the natural tooth root being replaced. The upper end can replicate the somewhat triangular cross section of the typical incisor, for example.

Figure 14:
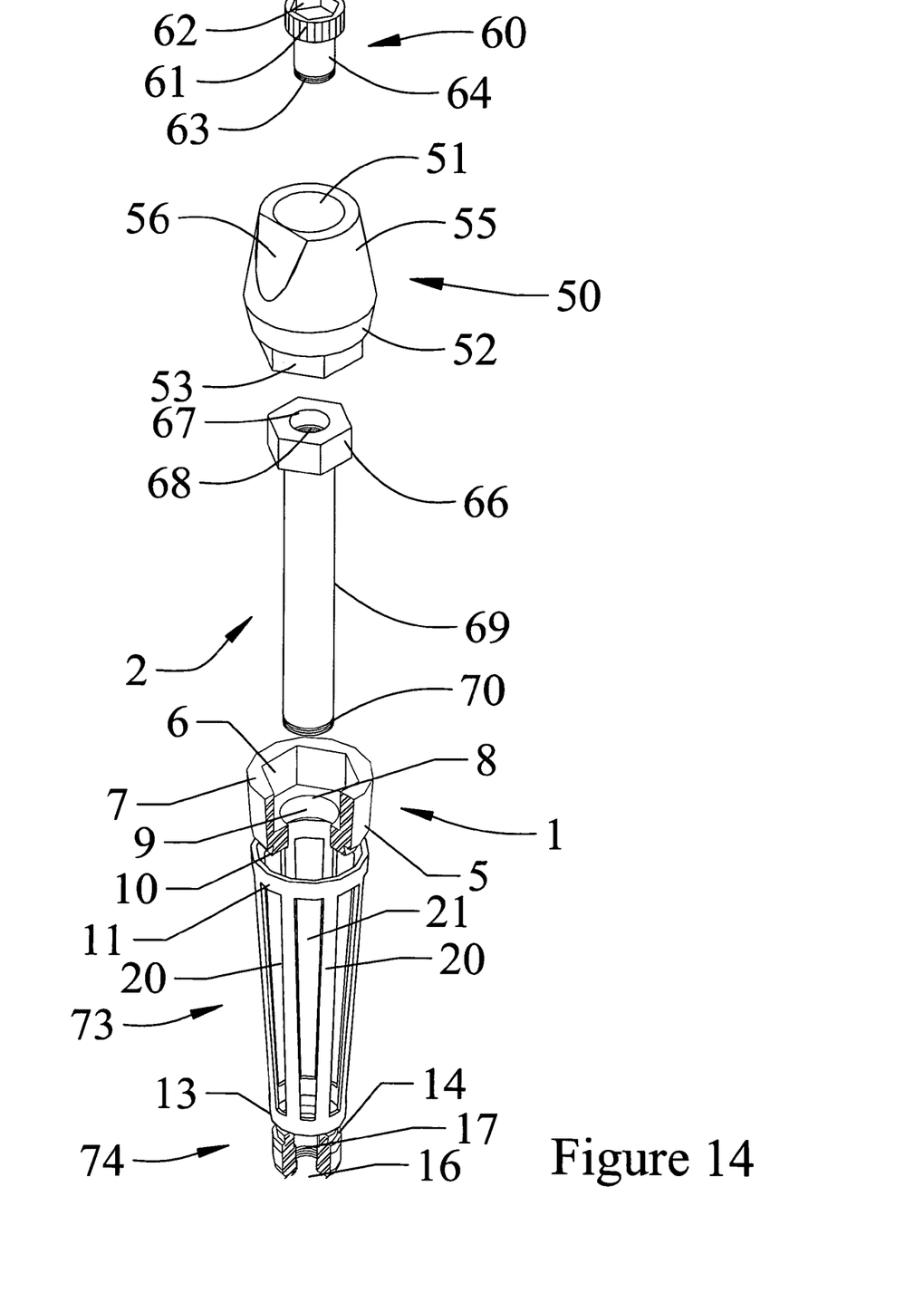
FIG. 14 is a perspective exploded view of an expandable, conical dental implant with hex head retaining screw.

FIG. 14 offers an exploded, perspective view of the expandable dental implant with conical shape to mimic the natural tooth being replaced. When implant screw 2 is tightened ribs 20 expand outward to lock the implant within a conical hole drilled in the bone. Abutment 50 fits conformally over hex head 66 and within recess 6 and is held in place by abutment screw 60.

In all of the embodiments described, the ribs 20 can be perforated to change the local flexibility and to allow for penetrating bone growth to better hold the implant in place. The edge of the rib can be scalloped with fingers to give the same locking action performed by thinning the edge of each rib. All or some of the metal alloy surface of the implant can be treated with conformal coatings that encourage good live bone adherence.

Figure 12:
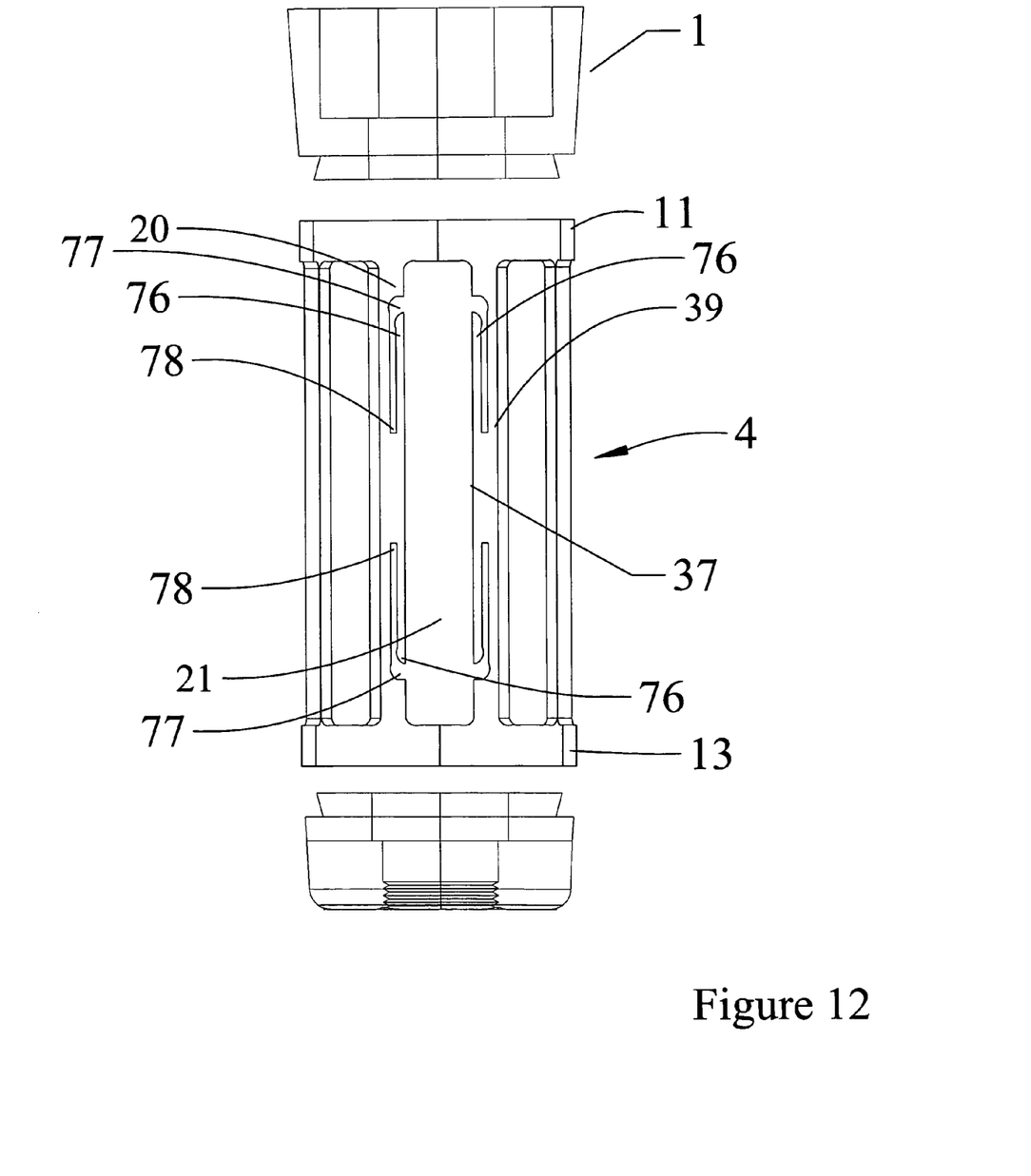
FIG. 12 an elevated front view of an implant having ribs with vanes.

FIG. 12 offers another embodiment of the invention, in which vanes or spines 76 are formed by etching a groove from open end 77 to internal end 78. These spines form an everted, almost vertical edge 37 that bites into the side walls of the hole drilled in the underlying bone when the expansion tube 4 is compressed. Edge 39 of rib 20 forms a continuous outward bow under compression while edge 37 with spines 76 press further into the side walls of the drilled hole to prevent rotational or translational motion.

Where photo-chemical milling techniques are given as a manufacturing technique, alternate methods including but not limited to laser machining and abrasive jet milling can be used to fabricate the expansion tube with equal precision.

What is claimed is:

1. A dental implant apparatus with expandable sides for locking into a predrilled hole in bone having an upper conformal socket, a hollow expansion tube with a wall having alternating ribs and open spaces, and a lower retaining nut;

said hollow expansion tube compressible along a major axis by tightening a retaining compression screw through said conformal socket, said expansion tube and said retaining nut;

and said ribs expanding outward upon the tightening of said retaining compression screw comprising said outwardly expanding ribs with a thinned portion on said ribs bowing outward to a greater distance that the thicker portion of said ribs to prevent rotation of said dental implant apparatus during installation and use, said thinned portions on said ribs alternating edges on alternate said ribs.

2. A dental implant apparatus, as described in claim 1, comprising outwardly expanding ribs with narrowed portions on said ribs bowing to a smaller radius than the un-narrowed portions of said ribs to prevent rotation of said dental implant apparatus during installation and use.

3. A dental implant apparatus, as described in claim 1, comprising outwardly expanding ribs with narrowed portions on said ribs bowing to a smaller radius than the un-narrowed portions of said ribs to prevent rotation of said dental implant apparatus during installation and use, said narrowed portions on said ribs alternating edges of alternate said ribs.

4. A dental implant apparatus, as described in claim 1, comprising outwardly expanding ribs, said ribs having edges that spiral about the central axis of said hollow expansion tube.

5. A dental implant apparatus, as described in claim 1, comprising a truncated conical shape to better mimic the normal root shape of a tooth.

6. A dental implant apparatus, as described in claim 1, comprising outwardly expanding ribs with spaces through portions on said ribs forming spines extending to a greater diameter than the un-spaced portions of said ribs to prevent rotation of said dental implant apparatus during installation.

7. A dental implant apparatus with expandable sides for locking into a predrilled hole in bone having an upper conformal socket, a hollow expansion tube with a wall having alternating ribs and open spaces, and a lower retaining nut;

said hollow expansion tube compressible along a major axis by tightening a retaining compression screw through said conformal socket, said expansion tube and said retaining nut;

and said ribs expanding outward upon the tightening of said retaining compression screw, wherein said outwardly expanding ribs comprise a notched edge on said ribs bowing outward to a greater distance than the unnotched edge of side ribs to prevent rotation of said dental implant apparatus during installation and use, said notched edges on said ribs alternating edges of alternate said ribs.

* * * * *